United States Patent
Perricone

(10) Patent No.: US 8,414,869 B2
(45) Date of Patent: Apr. 9, 2013

(54) MELANIN PROMOTING TOPICAL COMPOSITION

(75) Inventor: Nicholas V. Perricone, Meriden, CT (US)

(73) Assignee: N.V. Perricone LLC, Meriden, CT (US)

( * ) Notice: Subject to any disclaimer, the term of this patent is extended or adjusted under 35 U.S.C. 154(b) by 91 days.

(21) Appl. No.: 12/957,016

(22) Filed: Nov. 30, 2010

(65) Prior Publication Data

US 2012/0134938 A1    May 31, 2012

(51) Int. Cl.
*A61K 8/00* (2006.01)
(52) U.S. Cl. .......................................... 424/59
(58) Field of Classification Search .................. None
See application file for complete search history.

(56) References Cited

U.S. PATENT DOCUMENTS

| | | | |
|---|---|---|---|
| 4,515,773 A | 5/1985 | Herlihy | |
| 5,061,480 A | 10/1991 | Marchese et al. | |
| 5,376,361 A | 12/1994 | Perricone | |
| 5,409,693 A | 4/1995 | Perricone | |
| 5,545,398 A | 8/1996 | Perricone | |
| 5,554,647 A | 9/1996 | Perricone | |
| 5,574,063 A | 11/1996 | Perricone | |
| 5,603,923 A | 2/1997 | Robinson et al. | |
| 5,643,586 A | 7/1997 | Perricone | |
| 5,709,868 A | 1/1998 | Perricone | |
| 5,879,690 A | 3/1999 | Perricone | |
| 6,051,244 A | 4/2000 | Perricone | |
| 6,191,121 B1 | 2/2001 | Perricone | |
| 6,296,861 B1 | 10/2001 | Perricone | |
| 6,437,004 B1 | 8/2002 | Perricone | |
| 6,979,459 B1 | 12/2005 | Perricone | |
| 7,037,512 B2 | 5/2006 | Perricone | |
| 7,226,608 B2 | 6/2007 | Perricone | |
| 7,438,896 B2 | 10/2008 | Perricone | |
| 2004/0126344 A1* | 7/2004 | Mahalingam et al. | 424/62 |
| 2005/0042186 A1 | 2/2005 | Zahner | |
| 2005/0175556 A1 | 8/2005 | Gupta | |
| 2009/0035241 A1* | 2/2009 | Cassin et al. | 424/63 |
| 2009/0087395 A1 | 4/2009 | Lin et al. | |
| 2010/0080761 A1* | 4/2010 | Herrmann et al. | 424/45 |
| 2010/0183527 A1* | 7/2010 | Moser et al. | 424/59 |

FOREIGN PATENT DOCUMENTS

| WO | 2007025264 A2 | 3/2007 |
|---|---|---|
| WO | WO 2007025264 * | 3/2007 |

OTHER PUBLICATIONS

Joshi et al "Involvement of Reactive Oxygen Species in the Oxidation of Tyrosine and Dopa to Melanin and in Skin Tanning", Biochemical and Biophysical Research Communications; vol. 142; No. 1, Jan. 15, 1987 p. 265-274.*
Thangapazham et al.; "Beneficial Role of Curcumin in Skin Diseases"; Advances in experimental medicine and biology; 2007 595:343-357.
Hearing et al., From Melanocytes to Melanoma: The Progression to Malignancy (book); 2006; Humana Press Inc., NJ at p. 581 (only p. 581 submitted).
Nyugen et al.; "Nonmelanoma Skin Cancer"; Curr Treat Opt Oncol 3:193-203 (2002).
Talalay et al.; "Sulforaphane Mobilizes Cellular Defenses that Protect Skin Against Damage by UV Radiation"; Proc Natl Acad Sci USA; 2007; 104(44): 17500-17505.
Cho, et al.; "Tanning, Skin Cancer, and Prevention: A Content Analysis of Eight Popular Magazines that Target Female Readers, 1997-2006"; Health Commun. Jan. 1, 2010; 25(1): pp. 1-17.
Pak, et al.; "The Role of DCT/TYRP2 in Resistance of Melanoma Cells to Drugs and Radiation"; From Melanocytes to Melanoma: The Progression to Malignancy; 2006; pp. 577-589.
International Search Report & Written Opinion of the International Searching Authority; Application No. PCT/US2011/059323; Issued: Apr. 5, 2012; Mailing Date Apr. 30, 2012; 8 pages.

* cited by examiner

*Primary Examiner* — Bethany Barham
(74) *Attorney, Agent, or Firm* — St. Onge Steward Johnston & Reens LLC

(57) ABSTRACT

The invention provides sunless tanning compositions for application to skin comprising an effective amount of at least one dopamine precursor, an effective amount of curcumin and a dermatologically acceptable carrier. Methods for preparation of said compositions are disclosed. When applied to the skin, the compositions may be used darken skin.

23 Claims, No Drawings

US 8,414,869 B2

MELANIN PROMOTING TOPICAL COMPOSITION

FIELD OF THE INVENTION

The present invention relates to compositions and methods of skin darkening (sunless tanning) compositions and methods of skin darkening based on dopamine precursors and curcumin. A method is provided for preparing these compositions.

BACKGROUND OF THE INVENTION

Tanned skin is a commonly desired aesthetic element of personal appearance. A tanned appearance is associated with looking healthy, youthful and generally more attractive.

The natural tanning process is triggered by exposure to sunlight, particularly, ultraviolet (UV) light, and occurs when the skin expresses the pigment melanin. Melanin serves a photoprotective function arising from its photochemical properties. It absorbs harmful UV rays and transforms the energy into heat. This prevents the indirect DNA damage which is associated with the formation of malignant melanoma and other skin cancers.

The ultraviolet frequencies responsible for tanning are often divided into the UVA and UVB ranges. UVA causes the release of preexisting melanin from the melanocytes to combine with oxygen (oxidize), which in turn creates the actual tan color in the skin. UVB induces increased melanin production. UVB exposure will result in a tan about 2 days after exposure. UVA, and particularly UVB, can cause the formation of reactive oxygen species which in turn damage DNA both directly and through various biochemical pathways. The harmful effects of UV radiation are well understood, and UV radiation has been linked to more cancers worldwide than any other carcinogen. Nyugen et al., Nonmelanoma skin cancer, Curr Treat Opt Oncol 3:193-203 (2002).

Tanning beds have been used to mimic the effects of sunlight. Tanning beds use several fluorescent lamps that have phosphor blends designed to emit UV in a spectrum that is effective to cause tanning. Most tanning beds emit mainly UVA radiation.

To avoid the risk of UV radiation associated with sunlight or tanning beds, products have been developed to provide a suntanned look without the UV radiation. Thus, sunless tanning products, including self-tanners and spray tans have been developed to provide the appearance of a tan.

Most of the sunless tanning products available are lotions and sprays that contain dihydroxyacetone (DHA) as the active ingredient. DHA reacts chemically with amino acid groups which are part of the dead layer of keratin on the skin surface. Various amino acids react differently to DHA, producing different tones of coloration from yellow to brown. The resulting pigments are called melanoidins. These are similar in coloration to melanin. The artificial tanning coloring resulting from use of DHA based products can vary in color and evenness depending on the characteristics of the user's keratin layer. In some artificial tanning products erythulose is used in addition to DHA. Erythulose works in the same way as DHA on the skin surface, but provides a different color range. Juglone, and lawsone have also been used as bronzing agents.

Other agents used to produce a sunless tan include skin surface coloring agents, such as synthetic dyes, natural colorants and iron oxides. These cosmetic approaches do not provide a satisfactory, natural-appearing, long-lasting tan. In addition, colorants can wash off or cause staining of fabrics, There are two principal types of melanin associated with skin coloration: eumelanin and pheomelanin. Eumelanin provides black or brown skin coloration, while pheomelanin provides pale pink skin and red hair coloration.

Melanin is produced from tyrosine by the enzyme tyrosinase (formed by melanocyte skin cells). Tyrosinase converts tyrosine into dihydroxyphenylalanine (l-dopa), and then into dopaquinone. Dopaquinone is then converted into eumelanin or phaeomelanin.

Products have been proposed which stimulate the production of melanin in the skin. For example, the use of melanin precursors such as tyrosine and the enzyme tyrosinase, which is required to catalyze the formation of melanin, have been proposed For example, U.S. Pat. No. 4,515,773 (Herlihy) is directed to compositions for tanning the human epidermis. The compositions contain a 10 mM to 1 M concentration of precursors such as tyrosine, phenylalanine and catechol derivatives distributed throughout a base along with the enzyme tyrosinase.

U.S. Pat. No. 5,061,480 (Marchese et al.), directed to skin tanning compositions, discloses compositions with tyrosine active ingredient working in synergy with a non-ionic surfactant (e.g., polyoxyethylene ethers and polyoxyethylene sorbitan fatty acid esters such as BRIJ, TWEEN or ARLACEL) to increase the rate of penetration into the skin. Addition of riboflavin or adenosine triphosphate is disclosed to accelerate the oxidation process which produces skin tanning pigment. The tyrosine or derivative of tyrosine is taught to be present at 0.2 to 0.5 weight percent.

However, such products have not been effective in providing meaningful sunless melanin production and have not been commercially successful.

U.S. Patent Publication 2005/0175556 (Gupta), the disclosure of which is hereby incorporated by reference, is directed to skin darkening compositions based on enhancement of melanin synthesis by tyrosinase enzyme. Gupta discloses topical skin darkening compositions comprising (i) at least one tyrosine substrate agent, (ii) at least one tyrosine activator agent, and optionally, a pharmaceutical carrier. All examples teach Mucuna prurience extract or dihydroxy phenylalanine (D- and L-dopa) as the tyrosinase substrates. Copper ATP and copper glutathione are taught as tyrosine activator agents.

However, there remains a need in the industry for sunless tanning compositions that are effective and do not require activation using synthetic compounds or metals. Desirably, sunless tanning compounds will be formulated using naturally-occurring plant-based compounds as the tyrosine activators.

SUMMARY OF THE INVENTION

The present invention provides sunless tanning compositions comprised of a synergistic combination of dopamine precursors and curcumin.

In one embodiment, a sunless tanning lotion for application to skin is provided comprising an effective amount of at least one dopamine precursor, an effective amount of curcumin, and a dermatologically acceptable carrier.

The dopamine precursor is selected from the group consisting of tyrosine, N-acetyl tyrosine and phenylalanine and is present from about 1 to about 30 percent by weight. In preferred embodiments, the dopamine precursor is present from about 5 to about 20 percent by weight and most preferably from about 10 to about 15 percent by weight.

The curcumin is present from about 0.05 to about 10 percent by weight. In preferred embodiments, the curcumin is present from about 1.0 to about 5 percent by weight and most preferably, about 2.0 percent by weight.

The dermatologically acceptable carrier may comprise any of sodium hyaluronate, phosphatidylcholine, isopropyl palmitate, cetearyl alcohol, glycerol monostearate, shae butter, squalane, silicone and dimethyl ethanolamine. The pH of the composition is in the range from about 2.5 to about 6.0. In preferred embodiments, the pH of the composition is in the range from about 3.0 to about 5.5 and most preferably, from about 3.8 to about 5.0.

In some embodiments, the composition may further comprise phenylisothiocyanate from about 0.5 to about 10.0 percent by weight. In preferred embodiments, the phenylisothiocyanate is present from about 1.0 to about 8.0 percent by weight and most preferably about 2.0 to about 5.0 percent by weight.

In a further embodiment, the composition may comprise any of a-hydroxy acids, caffeine, vitamin D3, quercertin, sulforaphanes, and a blend of magnesium aspartate, zinc gluconate, and copper gluconate.

In yet another embodiment, the invention provides a sunless tanning composition comprising about 10 to about 15 percent by weight dopamine precursor, about 1 to about 3 percent by weight curcumin and about 4 to about 6 percent by weight phenylisothiocyanate, the balance being a dermatologically acceptable carrier, and wherein said dopamine precursor is selected from the group consisting of tyrosine, N-Acetyl tyrosine, phenylalanine, and mixtures thereof.

Additionally, the invention provides a method for preparing a sunless tanning composition comprising a water phase, an oil phase, an aqueous DMAE mixture, dopamine precursors, curcumin, and preservatives. The compositions are prepared by adding the water phase to the oil phase; mixing the water phase with the oil phase; cooling to 38-40° C.; adding the DMAE mixture at temperature of about 38° C.; adding the dopamine precursors and curcumin to the resulting mixture at a temperature of about 35° C.; and homogenizing. Following, preservatives are added and the composition is q.s.'d to 100.00% with water.

In a further embodiment, a method of darkening skin is provided. The method comprises the step of administering to the skin an effective amount of at least one dopamine precursor and curcumin acting in synergy with said dopamine precursor to upregulate melanin production. In this embodiment, the dopamine precursor may be present from about 10 to about 15 percent by weight and the curcumin from about 1.0 to about 5 percent by weight.

DETAILED DESCRIPTION OF THE INVENTION

Tyrosine (Tyr) is a non-essential amino acid that is synthesized from the amino acid phenylalanine (Phe). It is found in many high protein food products such as soy products, chicken, turkey, fish, peanuts, almonds, avocados, milk, cheese, yogurt, cottage cheese, lima beans, pumpkin seeds, and sesame seeds. The conversion of Phe to Tyr is catalyzed by the enzyme phenylalanine hydroxylase, a monooxygenase. This enzyme catalyzes the reaction causing the addition of a hydroxyl group to the end of the 6-carbon aromatic ring of phenylalanine, such that it becomes tyrosine. While tyrosine is hydrophobic, it is significantly more soluble than phenylalanine.

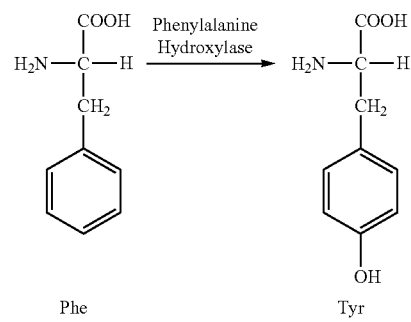 [SMILES: NC(Cc1ccccc1)C(=O)O ; NC(Cc1ccc(O)cc1)C(=O)O]

Tyrosine absorbs ultraviolet radiation and contributes to the absorbance spectra of proteins. Tyrosine is also a building block for several important neurotransmitters, such as dopamine (dopa) and helps produce melanin. There are two types of melanins: pheomelanin (yellow, red) and eumelanin (black, brown).

A biosynthetic pathway for the production of melanin is shown below.

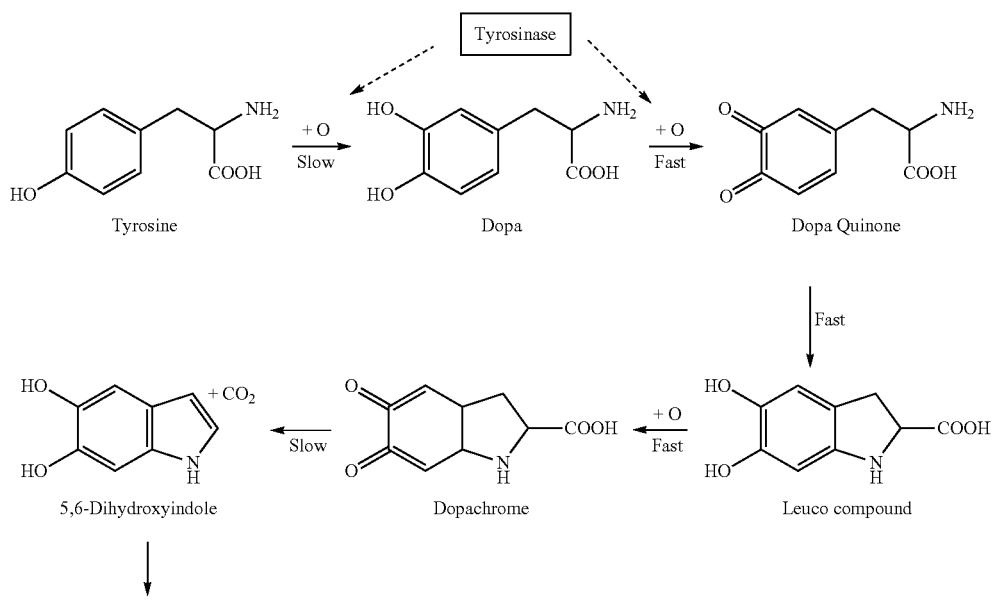

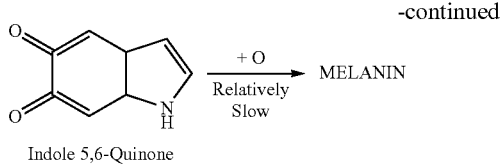

Indole 5,6-Quinone

The first two steps of the biosynthetic pathway for both eumelanins and pheomelanins are catalyzed by tyrosinase. Tyrosinase is a copper-based enzyme that catalyzes the oxidation of phenols (such as tyrosine) which in turn produce melanin and other pigments. The two copper atoms within the active site of tyrosinase enzymes interact with dioxygen to form a highly reactive chemical intermediate that then oxidizes the substrate. Tyrosinase also mediates the oxidation of 5,6-dihydroxyindole to indole-5,6-quinone. Although tyrosinase plays a role in the conversion of Tyr to dopa, it has recently been shown that formation of dopa from tyrosine occurs largely from non-enzymatic pathways. See Hearing et al., *From Melanocytes to melanoma: the progression to malignancy* 2006 Humana Press Inc., NJ at p. 581.

Dopaquinone can combine with cysteine by two pathways to produce benzothiazines and pheomelanins:

Dopaquinone+cysteine→5-S-cysteinyldopa→benzothiazine intermediate→pheomelanin

Dopaquinone+cysteine→2-S-cysteinyldopa→benzothiazine intermediate→pheomelanin

Alternatively, dopaquinone can be converted to leucodopachrome and follow two more pathways to the eumelanins:

Dopaquinone→leucodopachrome→dopachrome→5,6-dihydroxyindole-2-carboxylic acid→quinone→eumelanin Dopaquinone→leucodopachrome→dopachrome→5,6-dihydroxyindole→quinone→eumelanin The present invention recognizes the role of phenylalanine and tyrosine in the production of melanin and provides compositions comprising dopamine precursors in combination with curcumin to facilitate the production of melanin in human skin. Compositions of the present invention may be used to provide pigmentation to skin without the harmful effects of the sun. The compositions of the invention may be prepared by combining a dopamine precursor with curcumin in a dermatologically acceptable carrier.

In accordance with the invention, the term "skin" refers to the epidermal and dermal layers of skin. The term "skin" when used herein is in the broad sense meaning the skin of the face, body, and neck.

For purposes of the present invention, the term "dopamine precursor" refers to phenylalanine, tyrosine and/or N-acetyl tyrosine.

As discussed, phenylalanine is a precursor to tyrosine. N-Acetyl Tyrosine is an acetylated derivative of L-tyrosine. Ordinary L-tyrosine is less stable and also less soluble in water, which may result in reduced bioavailability. Acetylation enhances the solubility and stability of the amino acid, and thus is desirable for water based formulations and also to enable penetration into the skin where it can interact with protein.

The dopamine precursors are used in conjunction with curcumin. Curcumin is the principal curcuminoid of the popular Indian spice turmeric, which is a member of the ginger family (Zingiberaceae). Curcumin acts as a free radical scavenger and antioxidant, inhibiting lipid peroxidation and oxidative DNA damage. Curcuminoids induce glutathione S-transferase and are potent inhibitors of cytochrome P450.

The effects of curcumin are enhanced in the present invention by dissolving curcumin in a water in oil emulsion, which is thought to increase its bioavailability.

While not wishing to be bound by any theory, it is believed that curcumin in the formulations of the invention simulates the conditions of stress usually associated with exposure to UV radiation, stimulating melanocyte production of melanin. The synergistic combination of dopamine precursor(s) and curcumin upregulate melanin production providing a tanning effect. Furthermore, unlike DHA, the compounds are not reactive with water and, therefore, are able to react with the inner and outer layers of the stratum corneum and the living skin tissue.

As noted, these ingredients can be formulated into a lotion, cream or gel or spray by utilization of different proportions of the ingredients and/or by inclusion of thickening agents such as gums or other forms of hydrophilic colloids. The preferred embodiment is a lotion. Another possible embodiment is a solution that may be spayed onto the skin in a fine mist. The lotions, creams, gel and solution are referred to herein as dermally or dermatologically acceptable carriers, and are formulated using conventional techniques known to those of ordinary skill in the art. The term "sunless tanning composition" as used herein shall mean the complete product, including the dopamine precursor(s), curcumin, the carrier, and any adjuvants, thickeners, excipients, etc. as described herein, which is applied to a person's skin.

The topical composition of the invention can contain additional ingredients commonly found in skin care compositions and cosmetics, such as, for example, tinting agents, emollients, skin conditioning agents, emulsifying agents, humectants, preservatives, antioxidants, perfumes, chelating agents, etc., provided that they are physically and chemically compatible with other components of the composition.

Preservatives include, but are not limited to, $C_1$-$C_3$ alkyl parabens sorbic acid and phenoxyenthanol, typically present in an amount ranging from about 0.1% to about 2.0% by weight percent, based on the total composition. A preferred preservative is ISP's Optiphen™ Plus, a liquid preservative formulation featuring a blend of phenoxyethanol, sorbic acid and an emollient base.

Emollients, typically present in amounts ranging from about 0.01% to 5% of the total composition include, but are not limited to, hydrocarbons, fatty esters, fatty alcohols, mineral oils, polyether siloxane copolymers, and mixtures thereof. Preferred emollients are squalane, shae butter and isopropyl palmitate.

Humectants, typically present in amounts ranging from about 0.1% to about 5% by weight of the total composition include, but are not limited to, polyhydric alcohols such as glycerol, polyalkylene glycols (e.g., butylene glycol, propylene glycol, dipropylene glycol, polypropylene glycol, and polyethylene glycol) and derivatives thereof, alkylene polyols and their derivatives, sorbitol, hydroxy sorbitol, hexylene glycol, 1,3-dibutylene glycol, 1,2,6-hexanetriol, ethoxylated glycerol, propoxylated glycerol, and mixtures thereof. A preferred humectants is shae butter.

Emulsifiers, typically present in amounts from about 0.5% to about 10% by weight of the composition, include, but are not limited to, stearic acid, cetyl alcohol, stearyl alcohol, steareth 2, steareth 20, acrylates/C10-30 alkyl acrylate crosspolymers, silicones, dimethylethanolamine (DMAE), phosphatidylcholine (PPC) and mixtures thereof. Preferred emulsifiers are sodium hyaluronate, Promulgen-D® (a mixture of 75% cetostearyl alcohol and 25% ethoxylate cetostearyl alcohol sold by Amerchol Corp.), Arlacel 165 (Glyceryl Stearate and PEG-100 Stearate sold by Croda Inc.) silicone (Dow Corning 200 Fluid, 350 CST), DMAE and Phosphlipon 90 G (phosphatidylcholine with 10% fatty acids sold by Phospholipid GmbH).

Chelating agents, typically present in amounts ranging from about 0.01% to about 2% by weight, include, but are not limited to, ethylenediamine tetraacetic acid (EDTA) and derivatives and salts thereof, dihydroxyethyl glycine, tartaric acid, and mixtures thereof.

Antioxidants, typically present in an amount ranging from about 0.02% to about 5% by weight of the composition, include, but are not limited to, butylated hydroxy toluene (BHT); vitamin C and/or vitamin C derivatives, such as fatty acid esters of ascorbic acid, particularly ascorbyl palmitate; butylated hydroanisole (BHA); phenyl-$\alpha$-naphthylamine; hydroquinone; propyl gallate; nordihydroquiaretic acid; vitamin E and/or derivatives of vitamin E, including tocotrienol and/or tocotrienol derivatives; calcium pantothenates; green tea extracts; mixed polyphenols; and mixtures of any of these. Particularly preferred antioxidants are those that provide additional benefits to the skin, such as the green tea extract quercetin.

Buffering agents are employed in many compositions. It is preferable for compositions of the present invention to be an acid media. Preferably, the amount of buffering agent is one that results in compositions having a pH ranging from about 2.5 to about 6.0, more preferably from about 3.0 to about 5.5, most preferably from about 3.8 to about 5.0. Typical buffering agents are chemically and physically stable agents commonly found in cosmetics, and can include compounds that are also adjunct ingredients such as citric acid, malic acid, and glycolic acid buffers. The preferred buffering agent is glycolic acid.

Some embodiments of this invention contain at least one other adjunct ingredient in addition to dopamine precursor(s) and curcumin, typically ranging from about 0.05 to about 10% by weight of the composition. Adjunct ingredients include, but are not limited to one or more of: isothiocyanates, caffeine, vitamin D3, lipoic acid; $\alpha$-hydroxy acids such as glycolic acid or lactic acid; ascorbic acid and its derivatives, especially fatty acid esters of ascorbic acid; or tocotrienols and tocotrienol derivatives and vitamin E compositions enriched with tocotrienols or tocotrienol derivatives. Preferred adjunct agents are glycolic acid, caffeine and Sepitonic™ M3 by Seppic, which contains magnesium aspartate, zinc gluconate and copper gluconate.

Especially preferred adjunct ingredients are isothiocyanates. Isothiocyanates are sulfur containing compounds. Many natural isothiocyanates from plants are produced by enzymatic conversion of mustard oils. In one preferred embodiment, the present invention uses wasabi mustard or extracts thereof, e.g. methylthiohexyl isothiocyanates obtained from wasabi mustard. Other embodiments of the invention may incorporate phenylisothiocyanate. Another possible embodiment may include sulforaphane, an isothiocyanate obtained from cruciferous vegetables such as broccoli. Isothiocyanates have been shown to inhibit carcinogenesis and tumorigenesis and as such are useful chemopreventive agents against the development and proliferation of cancers. Talalay et al., Sulforaphane mobilized cellular defenses that protect skin against damage by UV radiation, *Proc Natl Acad Sci USA* 2007 104(44):17500-17505.

Additional ingredients and methods as disclosed in my U.S. Pat. Nos. 5,376,361; 5,409,693; 5,545,398; 5,554,647; 5,574,063; 5,643,586; 5,709,868; 5,879,690; 6,051,244; 6,191,121; 6,296,861; 6,437,004; 6,979,459; 7,037,512; 7,226,608; and 7,438,896, which are hereby incorporated by reference, may also be used.

Generally in the practice of methods of the invention, the topical composition is topically applied to the skin areas, such as that of the body and face, at predetermined intervals, it generally being the case that gradual color development is noted with each successive application. Insofar as has been determined based upon clinical studies to date, no adverse side effects are encountered.

It is an advantage of the present invention that a deep coloring is produced in the pigment layer of the epidermis, and unlike DHA which only colors the dead cell layer, the coloring is not rapidly lost through natural exfoliation processes. It is also an advantage of the present invention that the compositions are water based. Harsher solvents which are commonly used in sunless tanning compositions, are not required. Thus, the compositions are safer, more stable and do not have the undesirable scent often associated with DHA based products.

The following examples further describe and demonstrate embodiments within the scope of the present invention. The examples are given solely for the purpose of illustration and are not to be construed as limitations of the present invention, as many variations thereof are possible without departing from the spirit and scope of the invention.

EXAMPLES

Example I and Example II are oil in water emulsions prepared by combing the following ingredients using conventional mixing techniques.

| Ingredients | Example I | Example II |
|---|---|---|
| | Weight Percent | |
| Phase 1 | | |
| Water | qs 100 | qs 100 |
| Sodium hyaluronate | 0.50 | 0.50 |
| Glycolic acid | 0.25 | 0.50 |
| Phospholipon 90-G | 0.50 | 0.50 |
| Phase 2 | | |
| Isopropyl palmitate | 3.00 | 3.00 |
| Promulgen-D | 3.50 | 3.50 |
| Arlacel 165 | 3.50 | 3.50 |
| Shae butter - unbleached | 0.50 | — |
| Squalane - olive | 0.50 | 0.50 |
| DC Fluid 200, 350 CST | 0.50 | 0.50 |
| Part 3 | | |
| DMAE | 1.00 | 1.00 |
| Water | 2.00 | 2.00 |

-continued

| Ingredients | Example I | Example II |
|---|---|---|
| | Weight Percent | |
| Part 4 | | |
| L-tyrosine | 10.00 | — |
| N-acetyl tyrosine | — | 10.00 |
| Caffeine | 0.10 | 1.00 |
| Vitamin D3 | 0.10 | 0.10 |
| Curcumin 98% | 2.00 | 2.00 |
| Phenylalanine | 5.00 | 5.00 |
| Phenylisothiocyanate | 2.00 | 5.00 |
| Quercetin 60% | — | 2.00 |
| Sulforafames | 0.20 | — |
| Sesquiterpenes | 0.10 | — |
| Part 5 | | |
| Sepitonic M3 | 2.00 | 2.00 |
| Optiphen Plus | 0.50 | 0.50 |

Formulation: In a suitable vessel, the Phase 2 ingredients are dispersed in the Phase 1 ingredients with stirring. The mixture is cooled to 38-40° C. and Phase 3 is added. When the temperature reaches about 35° C., Phase 4 ingredients are added. The resultant mixture is homogenized for approximately 30 minutes. The mixture is sweep mixed and Phase 5 is added, if necessary.

The resulting lotions have a pH of about 3.8 to 5.0, exhibit good physical and chemical stability, deep color development characteristics, and are useful for topical application to human skin to provide a sunless tan.

In preliminary tests of the effectiveness of the formulations of Examples I and II, both were found to be effective of inducing sunless tanning, with the formulation of Example I providing noticeable skin darkening results with once-daily application after about 4 weeks, and the formulation of Example II providing noticeable skin darkening results with once-daily application after about 3 weeks. The present invention thus includes methods of darkening skin by administering to the skin an effective amount of at least one dopamine precursor and curcumin acting in synergy with said dopamine precursor to upregulate melanin production.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A sunless tanning composition for application to skin comprising: a melanin modulator that consists essentially of an effective amount of at least one dopamine precursor selected from tyrosine, N-Acetyl tyrosine and phenylalanine, and an effective amount of curcumin and a water-based dermatologically acceptable carrier.

2. The composition of claim 1, wherein the dopamine precursor is present from about 1 to about 30 percent by weight of the tanning composition.

3. The composition of claim 2, wherein the dopamine precursor is present from about 5 to about 20 percent by weight of the tanning composition.

4. The composition of claim 3, wherein the dopamine precursor is present from about 10 to about 15 percent by weight of the tanning composition.

5. The cosmetic composition of claim 1, wherein the dopamine precursor is N-Acetyl tyrosine.

6. The composition of claim 1, wherein the dopamine precursor is a combination of N-Acetyl tyrosine and phenylalanine.

7. The composition of claim 1, wherein the curcumin is present from about 0.05 to about 10 percent by weight of the tanning composition.

8. The composition of claim 7, wherein the curcumin is present from about 1.0 to about 5 percent by weight of the tanning composition.

9. The composition of claim 8, wherein curcumin is present at about 2.0 percent by weight of the tanning composition.

10. The composition of claim 1, further comprising phenylisothiocyanate.

11. The composition of claim 10, wherein the phenylisothiocyanate is present from about 0.5 to about 10.0 percent by weight of the tanning composition.

12. The composition of claim 11, wherein the phenylisothiocyanate is present from about 1.0 to about 8.0 percent by weight of the tanning composition.

13. The composition of claim 12, wherein the phenylisothiocyanate is present from about 2.0 to about 5.0 percent by weight of the tanning composition.

14. The composition of claim 1, wherein the dermatologically acceptable carrier comprises one or more agents selected from the group consisting of: sodium hyaluronate, phosphatidylcholine, isopropyl palmitate, cetearyl alcohol, glycerol monostearate, shae butter, squalane, silicone and dimethyl ethanolamine.

15. The composition of claim 1 further comprising one or more agents selected from the group consisting of: α-hydroxy acids, caffeine, vitamin D3, quercertin, sulforaphanes, and a blend of magnesium aspartate and zinc gluconate and copper gluconate.

16. The composition of claim 1, wherein the pH of the composition is in the range from about 2.5 to about 6.0.

17. The composition of claim 16, wherein the pH of the composition is in the range from about 3.0 to about 5.5.

18. The composition of claim 17, wherein the pH of the composition is in the range from about 3.8 to about 5.0.

19. The composition of claim 1, wherein the composition is a lotion.

20. A sunless tanning composition comprising:
about 10 to about 15 percent by weight dopamine precursor;
about 1 to about 3 percent by weight curcumin; and
about 4 to about 6 percent by weight phenylisothiocyanate;
the balance being essentially water, wherein said dopamine precursor is selected from the group consisting of tyrosine, N-Acetyl tyrosine, phenylalanine, and mixtures thereof.

21. A method for preparing a water-based sunless tanning composition comprising a water phase, an oil phase, an aqueous DMAE mixture, an effective amount of a dopamine precursor selected from tyrosine, N-Acetyl tyrosine and phenylalanine, an effective amount of curcumin, and preservatives, comprising the steps of: adding the water phase to the oil phase; mixing the water phase with the oil phase; cooling to 38-40° C.; adding the DMAE mixture at temperature of about 38° C.; adding the dopamine precursors and curcumin to the resulting mixture at a temperature of about 35° C.; homogenizing; adding preservatives; and q.s. to 100.00 with water.

22. A method of darkening skin, the method comprising the step of administering to the skin a water-based composition comprising an effective amount of at least one dopamine precursor selected from tyrosine, N-Acetyl tyrosine and phenylalanine and an effective amount of curcumin acting in synergy with said dopamine precursor to upregulate melanin production.

23. The method of claim 22, wherein the dopamine precursor is present from about 10 to about 15 percent by weight and the curcumin is present from about 1.0 to about 5 percent by weight.

* * * * *